United States Patent [19]

Snyder

[11] 4,274,967
[45] Jun. 23, 1981

[54] CHROMATOGRAPHIC APPARATUS AND METHOD

[75] Inventor: Lloyd R. Snyder, Yorktown Heights, N.Y.

[73] Assignee: Technicon Instruments Corporation, Tarrytown, N.Y.

[21] Appl. No.: 97,463

[22] Filed: Nov. 26, 1979

Related U.S. Application Data

[63] Continuation-in-part of Ser. No. 922,712, Jul. 7, 1978, Pat. No. 4,204,952, and Ser. No. 77,420, Sep. 20, 1979.

[51] Int. Cl.³ ............................................. B01D 15/08
[52] U.S. Cl. ........................................ 210/659; 55/67; 55/386; 210/198.2
[58] Field of Search .................. 55/67, 386; 210/31 C, 210/198 C

[56] References Cited

U.S. PATENT DOCUMENTS

| 3,422,665 | 1/1969 | Haase | 55/386 |
| 3,698,156 | 10/1972 | Dirian | 55/67 |
| 3,917,531 | 11/1975 | Magnussen | 210/198 C |
| 4,001,111 | 1/1977 | Geissler | 55/67 |
| 4,054,430 | 10/1977 | Valentin et al. | 55/67 |

Primary Examiner—John Adee
Attorney, Agent, or Firm—S. P. Tedesco

[57] ABSTRACT

An apparatus and method for increasing the throughput of a chromatographic system by passing several samples in seriatim through tandemly connected first and second chromatographic columns. The eluant from the first column is sampled, or fractionated, and fractions of each of the samples are passed through the second column for further separation. A switching of the sampling valve, disposed between the first and second columns, effects such fractioning. The pumping rate for the second column may be different from that of the first column and allows that two or more sample fractions can occupy the second column concurrently. Column efficiency or separation power of the system can be further increased by continuously recycling the fractions through the second column or passing such fractions through a third column which forms a continuous cyclic flow path with the second column via appropriate valve switching. Recycling can be continued until complete separation is achieved.

14 Claims, 11 Drawing Figures

CHROMATOGRAPHIC APPARATUS AND METHOD

RELATED APPLICATIONS

This application is a continuation-in-part of the previously filed applications entitled: "Chromatographic Apparatus and Method"; Ser. No. 922,712; filed July 7, 1978, now U.S. Pat. No. 4,204,952; and "Chromatographic Apparatus "; Ser. No. 077,420; filed Sept. 20, 1979, both assigned to a common assignee.

FIELD OF THE INVENTION

The present invention relates to a chromatographic system, both liquid and gas, having an improved throughput, and column efficiency.

BACKGROUND OF THE INVENTION

In chromatographic systems of the prior art, a single sample to be separated wastefully occupied only a small portion of a chromatographic column. A second sample was not introduced into such column until the first sample had been completely eluted. Accordingly, chromatographic separation of samples was an inefficient and time-consuming procedure. The present invention contemplates a much more efficient use of a chromatographic column. This increased efficiency is achieved by initially separating each of a number of samples fed seriatim into a first column into its individual components on a coarse basis. The eluant passing from the first column is sampled, so as to pass particular fractions of each sample seriatim through a second column, wherein a complete separation of the constituents is effected. This technique provides a passage of many sample fractions through the system concurrently. The over-all result is a dramatic increase in the throughput of the chromatographic system. The column efficiency or separation power of such a system is also improved dramatically by recycling in a continuous fashion those fractions eluting through the second column or passing such fractions through a third column which forms a cyclic flow path with the second column.

PRIOR ART

The art of chromatography is highly prolific and varied in its procedures and apparatuses for purifying and analyzing samples. Some prior systems used multiple stages to separate complex samples exhibiting a difficulty towards separation. Such systems used two or more columns arranged in series and packed with different column packings. Description of such systems can be found in the articles to: "TWO-STAGE GAS-LIQUID CHROMATOGRAPHY", M. C. Simmons and L. R. Snyder, *Analytical Chemistry*, Vol. 30, page 32, January, 1958, and "GAS CHROMATOGRAPHY," Orion Edwin Schupp III, *Technique of Organic Chemistry*, Vol. XIII, page 251, 1968. These prior art systems feature a switching valve between the two columns to select one or more adjacent bands for preseparation by a short column and further separation by a long column, not unlike the inventive system. However, these systems do not provide an increase in throughput. It is characteristic of such systems that only one sample is passing through the system at any one time. The principle of operation of these prior art systems is differing separation selectivity in each column.

The Schupp article discusses special problems with dilute samples, wherein a pre-column is used followed by a switching valve serially connecting a second column which may be packed with the same material. Low-boiling components of the sample are allowed to vent to waste in the first column. The temperature of the pre-column is raised to effect faster elution of sample components of interest, and a normal separation of the residual sample results. The object of this technique is to vent large volumes of solvent or other low-boiling compounds of no interest to waste prior to initiation of the main separation. This method eliminates the adverse effects produced by these materials upon column separation. High-boilers, which require a long elution time, are held on the first column until separation is completed. They are removed from the first column by means of back-flushing or other well-known techniques.

Another multiple column system is illustrated in the reference to "COMPARISONS OF NORMAL ELUTION, COUPLED-COLUMNS, AND SOLVENT, FLOW OR TEMPERATURE PROGRAMMING IN LIQUID CHROMATOGRAPHY", L. R. Synder, *Journal of Chromatographic Science*, Vol. 8, page 692, December, 1970. Such system is particularly useful for difficult-to-analyze samples containing many constituents. Two or more columns are connected in parallel and/or series and have different retention strengths. Such system is adapted to divert unretained sample components that elute early from the weak-retention-strength column to the strong-retention-strength column. This will provide resolution of weakly-retained components. This procedure is similar in effect to such other procedures as gradient elution, temperature programming and flow programming.

In such system, only one sample is in the system at any given time. Accordingly, the throughput of this system is not particularly high.

Another technique features a continuous chromatographic refining of a sample. Continuous separation of a single sample is done for the purposes of preparing large quantities of pure material. Such a method is shown in the reference to "CONTINUOUS CHROMATOGRAPHIC REFINING USING A NEW COMPACT CHROMATOGRAPHIC MACHINE", P. E. Barker and S. Al-Madfai, *Journal of Chromatographic Science*, Vol. 7, page 426, July, 1969; R. A. Findlay, U.S. Pat. No. 3,002,583, issued Oct. 3, 1961; and the Barker et al U.S. Pat. No. 4,001,112, issued Jan. 4, 1977. These latter three references teach a refining or purifying of a constituent by chromatographic procedures, and are not concerned with increasing the throughput of the system. Discrete samples are not introduced successively or travel concurrently through a separatory column.

The patents to J. Hrdina, U.S. Pat. No. 3,373,872, issued Mar. 19, 1968 and U.S. Pat. No. 3,508,880 issued Apr. 28, 1970, depict chromatographic systems having more than one column operated by a single pump. These patents, like the previous references, do not relate to passing a multiplicity of discrete samples through a column or system at any one given time.

SUMMARY OF THE INVENTION

As aforementioned, the present invention seeks a dramatic increase in the throughput of a liquid or gas chromatographic system. First and second columns are arranged in tandem and may be packed with the same or different material. A switching, or sampling, valve is located between the columns to fractionate each sample eluant passing seriatim from the first column. The fractional eluant may contain several adjacent bands of compounds which are fed to the second column for a more complete separation. Unwanted eluants are discarded to waste by the switching valve as they precede or follow the bands of interest. In other words, the switching valve takes a cut or fraction from each sample passing from the first column and feeds such fraction to the second column.

As the second column is fed only a small fraction of the sample, one or more fractions of different samples can be passed therethrough concurrently and separation is more efficiently effected.

A subsequent sample of similar constituents is now fed through the first column as remaining material from the prior sample leaves the first column. The second and subsequent samples are fractioned similarly to the first sample. The process will feed the discrete sample fractions into the second column at a controlled rate. When the first sample fraction has moved a discrete distance along the second column, a subsequent sample fraction is passed to the second column, such that a string of adjacent sample fractions is moved along the second column concurrently. This dramatically improves the throughput of the chromatographic system.

The injection rate and volume of different sample fractions fed to the second column are controlled in respect of the rate of flow through the second column. Accordingly, the constituent of interest in each sample fraction will be separated but will not overlap with other adjacent constituents when eluted from the second column. Furthermore, the introduction of samples into the first column may be synchronized with the introduction of sample fractions into the second column. Thus, a continuous process of analyzing discrete adjacent samples is achieved wherein discrete non-overlapping constituents of interest contained in the eluants of each sample fraction are obtained.

A very great increase in column efficiency or separation power can also be achieved for the above-mentioned system by using the technique of recycle chromatography. For example, see L. R. Snyder and J. J. Kirkland, "Introduction to Modern Liquid Chromatography", 2nd Edn., Wiley-Interscience, New York, 1979, pp. 519–522. Fractions eluting from the second column are loaded into one or more recycle columns. The number of fractions loaded into the recycle columns would depend upon column length and the number of recycling operations to be achieved. Once this fraction-loading has been accomplished, the valving for the system would be set to allow continuous recycling of sample fractions through the second column or passing such fractions through a third or more columns, until the necessary separation of each sample fraction has been achieved. The separated fractions can then be diverted to a suitable detection means.

Such a recycling, while taught by the prior art as applicable to single or individual sample separation, is not obvious in combination with the above throughput system wherein more than one of a string of sample fractions are simultaneously occupying the recycle columns. This is so, because of the complexities of flow induced by a multiplicity of fractions, whose separation causes a spreading or possible overlap within the columns whose overlap must be carefully controlled to prevent overlapping of the eluted constituents.

OBJECTS OF THE INVENTION

It is an object of this invention to provide an improved chromatographic method and apparatus;

It is another object of the invention to provide a chromatographic system having an improved throughput as well as improved column efficiency or separating power; and It is a further object of this invention to provide a continuously fed chromatographic system wherein a plurality of discrete fractions of samples are passing through a chromatographic column of the system concurrently.

BRIEF DESCRIPTION OF THE DRAWINGS

These and other objects of the invention will be better understood and will become more apparent with reference to the accompanying drawings, in which:

FIG. 2a–2d are various schematic diagrams of compounds travelling along separatory columns.

FIGS. 6a–6c depict various schematic diagrams of fractions traveling along the recycling columns of FIG. 5.

DETAILED DESCRIPTION

The present invention contemplates the passage of a series of samples through a first chromatographic column for crudely separating the constituents thereof. A fraction of each sample eluant passing from the first column is directed to a second column, which completes the separation. Passage of such fractions through the second column is effected at a controlled rate, to ensure that the particular constituents of interest in each fraction do not overlap (or otherwise are sufficiently separated) when eluted from the second column. The throughput of the system is substantially increased, by passing a plurality of fractions of different samples through the second column concurrently.

The apparatus of the invention features: a first chromatographic column; means to pass a series of samples into the first column; a second chromatographic column; and means to pass the fractions of each sample eluant from the first column into the second column at a controlled rate to ensure that constituents of interest of each sample fraction eluting from the second column will be sufficiently separated for purposes of analysis.

Figure 1:
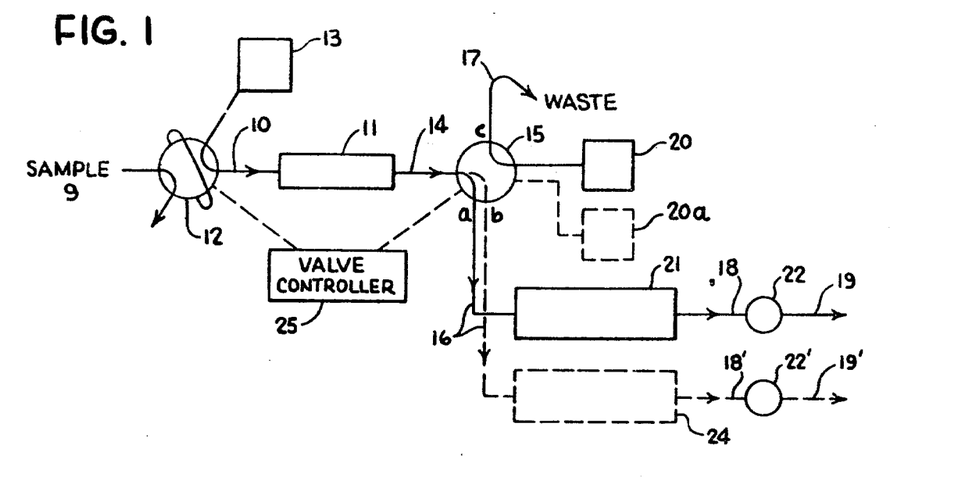
FIG. 1 is a schematic diagram of a chromatographic system of this invention.

Now referring to FIG. 1, a sample 9 is introduced, as indicated by arrow 10, along with a solvent into a first chromatographic column 11 by means of an injection valve 12 and a continuously pumping of high pressure pump 13. The sample usually contains several compounds, one or more of which are particular constituents of interest to be ultimately separated from the other compounds and analyzed. The sample 9 passes through column 11, under the impetus of pump 13, and the eluant passing from column 11, as indicated by arrow 14 is fed to a switching or sampling valve 15. The purpose of valve 15 is to allow a cut of the sample or otherwise separate a fraction containing the particular constituent of interest from other compounds in the sample. The switching valve 15 feeds such constituent under the impetus of high pressure pump 13, as indicated by arrow 16, from outlet a to a second chromatographic column 21. The fraction obtained by valve 15 is a crude cut of sample 9 that contains the constituent of interest, along with other closely-eluting compounds, which are not completely separated. Accordingly, a further separation by column 21 is required. Continuously operating high pressure pump 20 supplies the impetus for driving each separated fraction through column 21 during further elution of column 11 by pump 13. Other portions of the eluant leaving column 11 which are not associated with the constituent of interest, are discarded from the system from outlet c of valve 15, as indicated by arrow 17. If desired, however, such portions may be further fractionated and passed to a third column 24 (shown in phantom) for separation and analysis of an additional constituent. Additional column 24 is connected to a second outlet b of valve 15, the outlet being connected to column 24 as shown. The fraction delivered from outlet b of valve 15 is fed onto column 24 under the impetus of pump 13, and subsequently driven through column 24 by high pressure pump 20a.

The fraction of the original sample 9 exiting column 21 and/or column 24 is fed (as indicated by arrows 18 and 18') to detectors 22 and 22', respectively. The eluant is then discarded, as indicated by arrows 19 and 19', respectively.

The detectors 22 and 22', respectively, may be photometers or spectrophotometers. Alternately, they can be refractometers, electrochemical detectors, fluorometers, or conductivity detectors, etc. The purpose of such detectors is to quantify, or otherwise measure the amount of the particular constituent of interest in the eluant passing the associated column.

The operation of the system will be described with respect to only column 21. However, such description will be operable in respect of additional columns, such as 24, included in the system. The structure of the system associated with column 21 bears close resemblance to many prior art systems. However, pumps 13 and 20, together with valve 15, have an essentially different operation and function than do their prior art counterparts. Pumps 13 and 20 operate to introduce their respective materials into columns 11 and 21, respectively, serially, and at rates which are synchronized and controlled to provide two important features: (1) a plurality of fractions are concurrently passed through column 21, and (2) the constituent of interest in each sample fraction eluted from column 21 is substantially completely separated and does not overlap with other concurrent constituents.

Figure 2A:
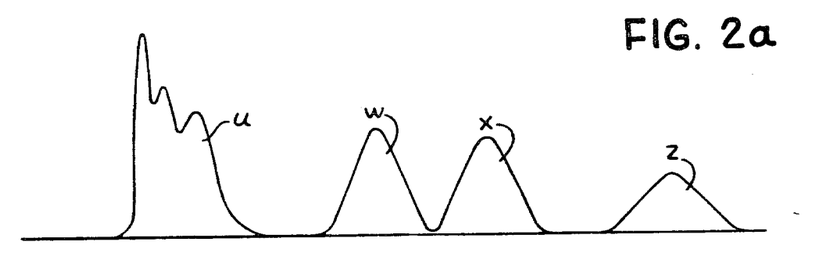
FIG. 2a shows the separation of compounds within a sufficiently long column equal in length to the short and long columns of FIG. 1, such that closely-eluting compounds "W" and "X" are completely separated.

To more fully understand the invention, reference is made to FIGS. 2a through 2d. FIG. 2a illustrates a complete separation of several constituents, "U", "W", "X" and "Z" in a sample. These constituents have been passed through a conventional chromatographic column having a length equal to the summed lengths of columns 11 and 21. "X" is designated (by hatching) as the particular constituent of interest to be analyzed.

Figure 2B:
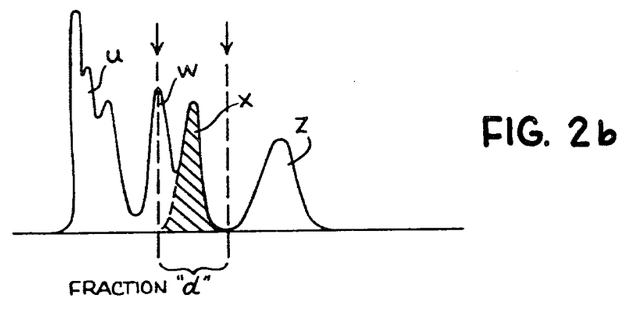
FIG. 2b depicts travel of compounds within the short column as shown in FIG. 1, such that closely-eluting compounds "W" and "X" are overlapping each other.
Figure 2C:
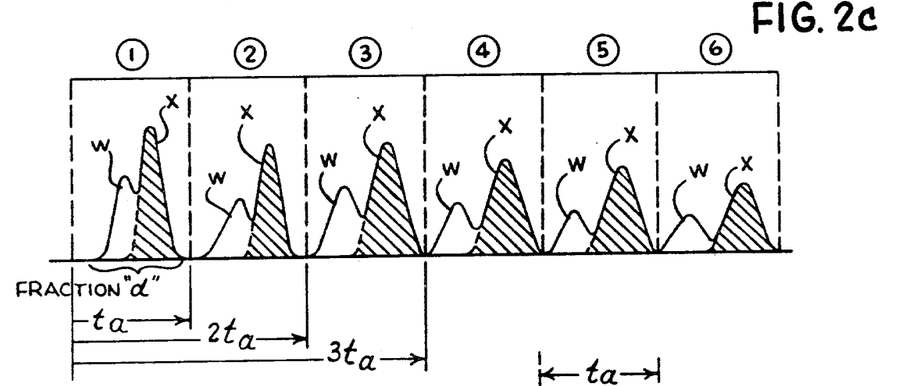
FIG. 2c illustrates a plurality of fractions or cuts ("d") taken from the short column (see FIG. 2b) which have been introduced to, and are passing through, the long column shown in FIG. 1.

If the system of FIG. 1 were operated using only column 11, the separation shown in FIG. 2b would result. As shown in FIG. 2b, the constituent of interest "X" is eluted with closely-eluting, overlapping constituent "W". Valve 15 of FIG. 1 selects the fraction designated "d", containing constituent "X" and an analyzing portion of "W". This selected fraction is retained in the system, and all other portions of the sample eluant are shunted to waste, as indicated by arrow 17, from outlet c. The fraction "d" should be sufficient to ensure that essentially all of the constituent "X" is passed to column 21. As aforementioned, the retained fraction "d" of each sample 9 is passed by valve 15 along outlet b to the second column 21. FIG. 2c illustrates the further separation of the fraction "d" along column 21. Fraction "d" will be seen to contain constituent "X" intermixed, or overlapping, with constituent "W". FIG. 2c illustrates in time lapse fashion, the separation of constituents "X" and "W" as the individual fraction "d" is passed through column 21. FIG. 2c can also be a representation of several fractions passing concurrently through column 21, as will be explained hereinafter.

Column 21 will be "imagined" (for purposes of description) as being divided into six separate sections or stages 1–6, as shown. The fraction "d" is introduced into column 21 at section 1 and passes through each succeeding stage until it reaches the final section 6. It will be seen from FIG. 2c, that each stage progressively separates the fraction constituents "W" and "X", such that, at the final section 6, "W" and "X" are substantially completely separated.

If only one fraction "d" of sample 9 was passed through column 21, the processing rate or dwell time through the system would be the same as if columns 11 and 21 were connected together and no fraction was taken.

While the present invention does not process an individual sample any faster than the prior art, i.e., the dwell time of each sample in the system is not reduced, the overall sample processing rate, or throughput, however, is increased. This is accomplished by passing a multiplicity of sample fractions "d" through column 21 concurrently and at a controlled rate. After a fraction "d" of a first sample has passed through column 21 for a time "$t_a$", for example, fraction "d" of a second sample can be introduced into the column without interfering with the first sample fraction. This will be seen to be true, since the first fraction will now start to occupy section 2 while the second fraction is entering section 1. At the end of time "$2t_a$", the first fraction will be fully occupying section 2, while the second fraction will be fully occupying section 1. A third fraction may now be introduced to section 1. At the end of time "$3t_a$", the first fraction will be occupying section 3, the second fraction will be within section 2, and the third fraction will be occupying section 1. This procedure can be continued until all sections of column 21 will be filled with fractions passing therethrough.

While column 21 is not divided into actual sections, the principle of passing several fractions into the column will be observed to be valid nonetheless. For example, it will be noted, that the space occupied by fraction "d" at any instant in section 1, is less than the distance necessary to traverse section 1 in time "$t_a$". However, fraction "d" will fully occupy all the space when it reaches section 6 due to expansion of constituents "X" and "W". In other words, the rate of introduction of sequential fractions must be controlled to adjust for expansion of the constituents as they pass through the column 21. Such control of the rate will provide that each successive sample fraction will not cause interference with other adjacent sample fractions within the columns. In other words, fraction "d" derived from different samples passed individually through column 11 is introduced and passed along column 21, in spaced, non-overlapping fashion. Also, under the impetus of pump 20, such fractions move concurrently along column 21 at a same rate, and the spacing is such that constituent "X" in each sample is fully separated when passed to detector 22 for measurement.

To achieve optimum performance, sample 9 is successively introduced into column 11 at a rate synchronized with the rate at which sample fractions "d" are passed into column 21. Accordingly, there is sufficient separation of the constituent "X" in the successive fractions leaving column 21. Synchronism is achieved by a valve controller (timer) 25, which may be a microprocessor. The microprocessor may also be used to control the recycling valves 41 and 42 of the system shown in FIG. 5, as will be explained hereinafter.

Figure 2D:
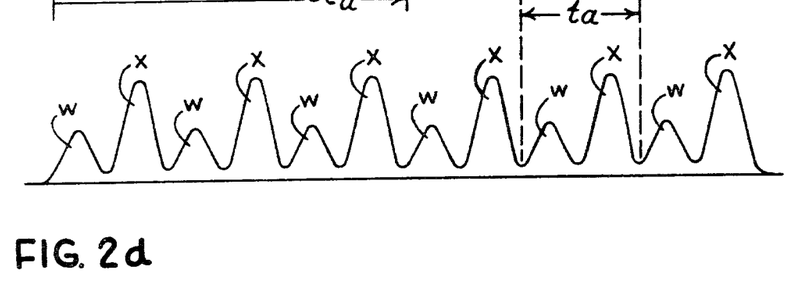
FIG. 2d shows the successive elution of compounds "W" and "X" of adjacent sample fractions emerging from the long column of FIG. 1 in accordance with the invention.

FIG. 2d shows the sequence of non-overlapping fractions "d" leaving column 21, when proper synchronism is achieved.

Figure 3:
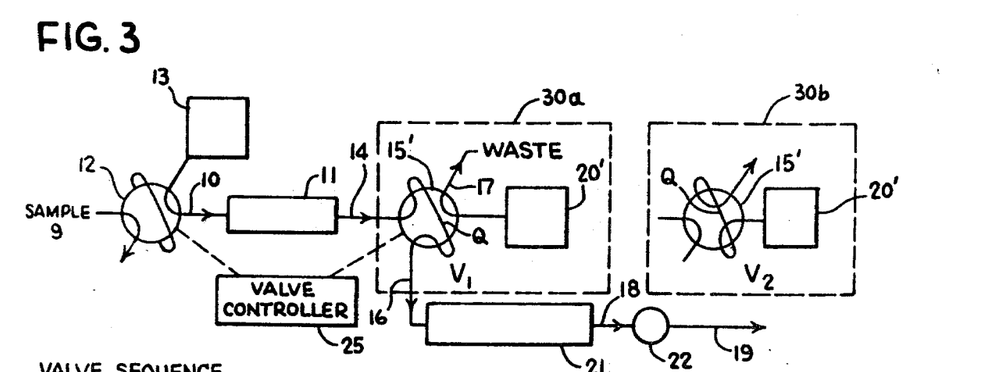
FIG. 3 depicts a schematic diagram of an alternate embodiment to the chromatographic system of FIG. 1.

The system diagram of FIG. 1 requires two high pressure pumps 13 and 20, respectively, to achieve the above-mentioned synchronism. Another embodiment requiring only one high pressure pump is shown in FIG. 3. In this embodiment, switching valve 15 is now replaced with a new switching valve 15' having a fraction-storage loop Q. This allows pump 20 (a high pressure pump) to be replaced by a low-pressure pump 20'.

Figure 4:
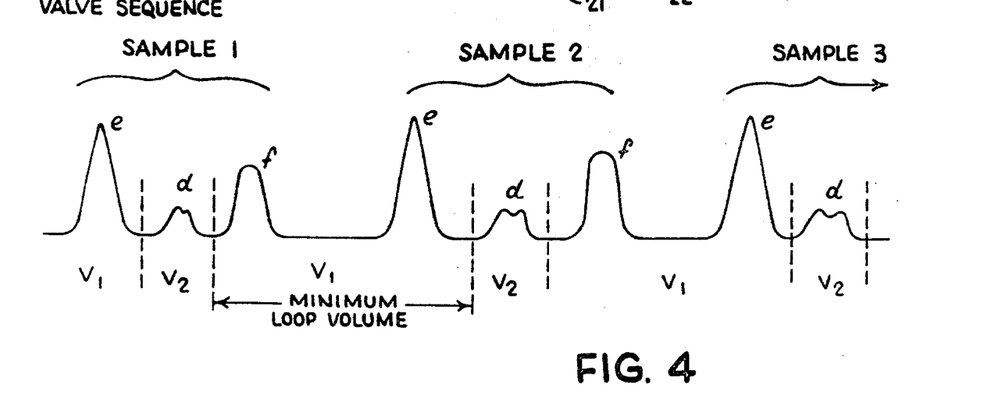
FIG. 4 illustrates a schematic diagram of the valve sequence for the embodiment shown in FIG. 3.

The dashed lined boxes 30a and 30b, respectively, show the different operating phases $V_1$ and $V_2$ of switching valve 15'. Also, the compositions of the eluant passing from column 11 in respect of three successive samples $S_1$, $S_2$, and $S_3$ is shown in FIG. 4. In FIG. 4, the proper phase of valve 15' in respect of the particular constituent fractions of each sample is shown.

Initially, the switching valve 15' is switched to phase $V_1$. This allows the fraction "e" (and in subsequent samples "f") to pass into the storage loop Q while the solvent from loop Q enters column 21. However, the loop is large enough that the fractions "e" and "f" entering it do not leave the loop until it has been switched to phase $V_2$. When a fraction of interest "d" elutes from column 11, the switching valve 15' is switched to position $V_2$, and simultaneously the holding loop is flushed with fresh solvent, thus sending the unwanted components (fractions "e" and "f") to waste and desired component "d" directly onto column 21. Note pump 20' is now used in a countercurrent mode to flush the loop. The switching valve 15' now returns to $V_1$ as soon as fraction "d" has been loaded into column 21, and the loop again collects unwanted material (fractions "e" and "f") until the next desired fraction "d" is eluted from column 11.

As long as the loop on switching valve 15' is large enough to hold the volume of sample eluting between the desired fractions in two successive samples (see FIG. 4) only the desired components reach column 21. The only requirement for the low pressure pump 20' is that it pump fast enough to completely flush the loop with fresh solvent during the time the switching valve 15' is in position $V_2$.

Several modifications to the above-described systems can be made within the purview and scope of this invention. For example, the invention contemplates using a first column 11, that is shorter than the second column 21. This may be modified, and both columns may be made of equal length.

While a typical set of compounds "U", "W", "X" and "Z" were elucidated in FIGS. 2a–2d, it is naturally to be understood that other sequences of compounds will work with this invention.

The packing material for both columns 11 and 21 is desirably made the same, but not necessarily identical. There may be situations where this may not be true, as may be exercised by those skilled in this art.

Additional columns such as column 24 may be added to separate other constituents from each sample, or as a means to further improve the throughput of the system. Where increased throughput is desired, the third column 24 may alternately receive fractions along with column 21. In this mode of operation, column 11 will be fed samples twice as fast as before.

Still another mode of operation could feature three tandemly arranged columns 11, 21 and 24 which make progressively finer cuts in the eluants. For this mode of operation, another switching valve will be required between columns 21 and 24, respectively.

Figure 5:
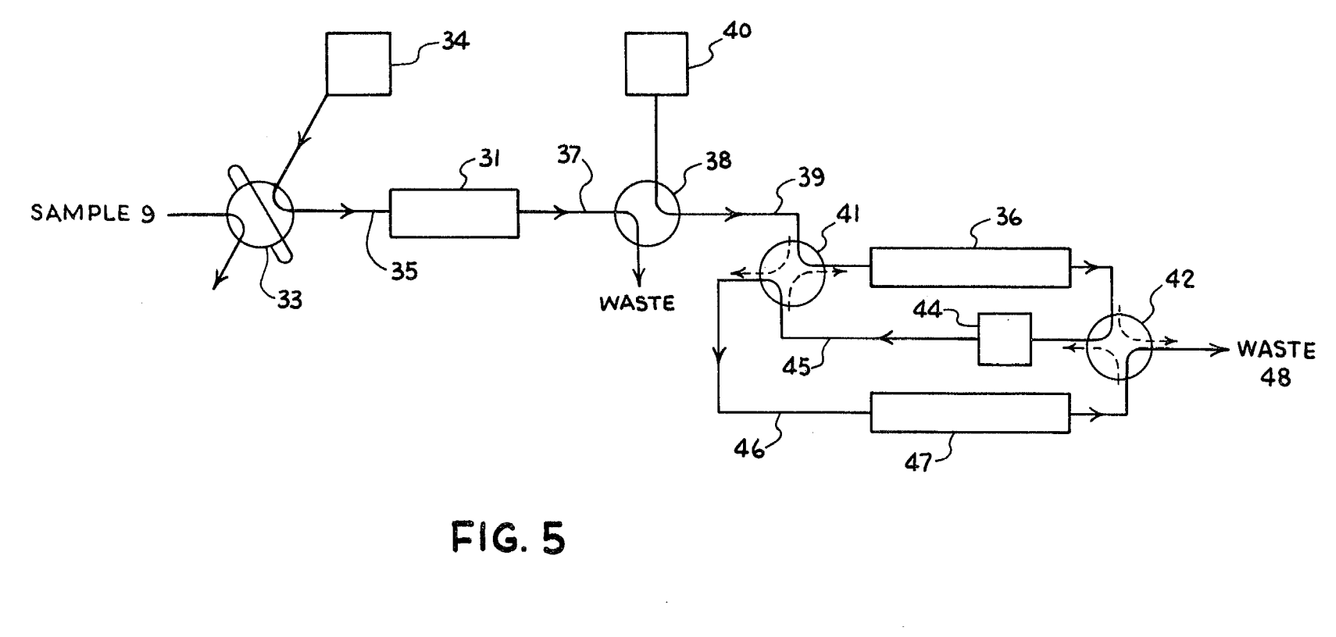
FIG. 5 illustrates a schematic diagram of a modified chromatographic system similar to that shown in FIG. 1, but having facility to recycle the eluant passing from the second column.
Figure 6A:
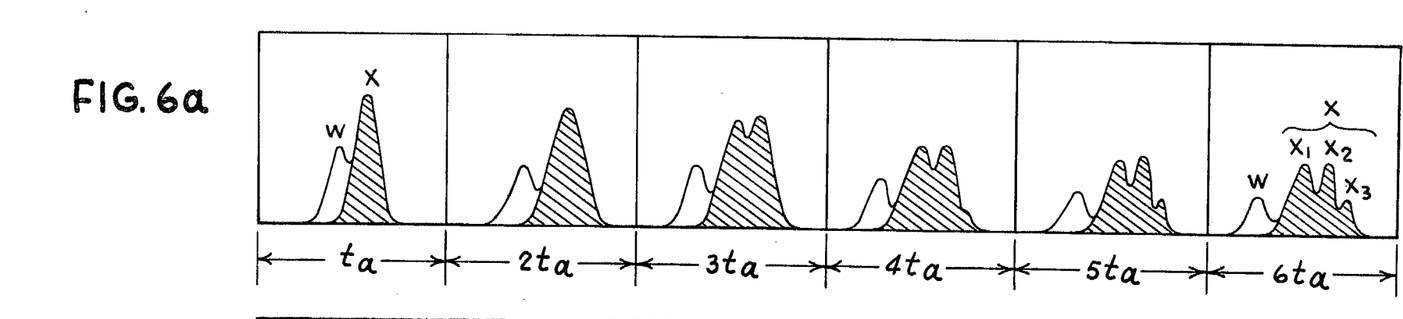
FIG. 6a shows sample fractions which are loaded on to the second column of the system of FIG. 5.
Figure 6B:
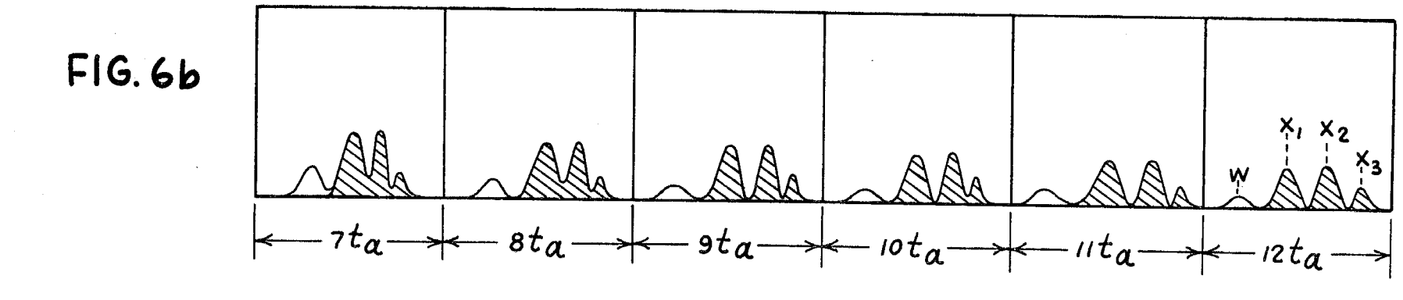
FIG. 6b depicts the samples fractions being loaded on to the third column of the system of FIG. 5.
Figure 6C:
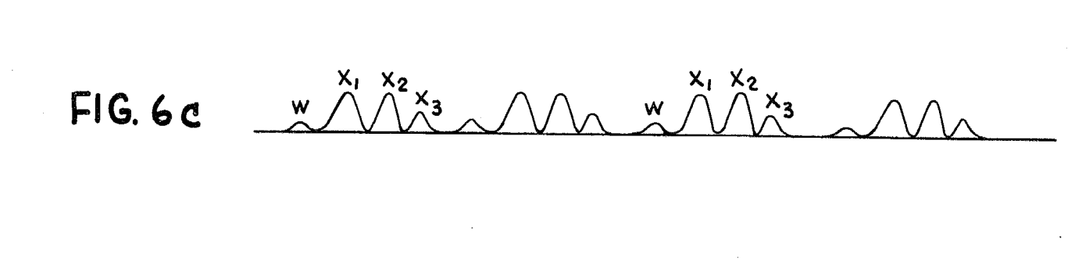
FIG. 6c shows the analyzer response to the recycled fractions eluting from the third column of FIG. 5.

Referring to FIGS. 5 and 6a–6c, another embodiment of the inventive chromatographic system is shown having a recycling capability. This recycling capability provides for a further increase in column efficiency or separation power when single-pass operation is unable to fully resolve the sample. For example, assume that the band "X" shown in FIG. 2a consists of three components "$X_1$"; "$X_2$"; and "$X_3$", which components are not fully resolved after passage of the sample through columns 11 and 21 of FIG. 1. FIG. 6a shows that band "X" is only partially separated into bands "$X_1$"; "$X_2$"; and "$X_3$" as the total sample fraction "X" approaches the end of the column 21. Further resolution of the sample can be achieved by recycling fractions "$X_1$"; "$X_2$"; and "$X_3$", using the apparatus of FIG. 5. In a recycling operation, a series of samples are first loaded onto a first column 31 of FIG. 5, in the same manner as was previously employed in the apparatus of FIG. 1. Each sample 9 enters the system via the sample-valve 33. Under the pumping-action of pump 34, the sample 9 leaves the sample-valve 33 and passes through the conduit 35 to enter the preprocessing or first column 31. The sample 9 is partially separated in column 31, as illustrated in FIG. 2b. A selected fraction containing band "X" is diverted into conduit 39 via switching-valve 38 and conduit 37 and enters a second column 36. Each sample fraction "X" is loaded into the second column 36 in a respective time interval "$t_a$" until the column is completely filled in time "$6t_a$" with sample fractions, as illustrated in FIG. 6a. During this period, the pump 40 continues to pump the mobile phase through valve 38 to waste. The further loading of sample-fractions "W" and "X" from column 31 onto column 36 is now discontinued, and switching valves 38, 41 and 42 are respectively positioned to load eluant from second column 36 onto third column 47 as shown in FIG. 5. Sample fractions "W"; "$X_1$"; "$X_2$"; and "$X_3$" pass under the influence of pump 40 through conduit 43, detector 44, conduit 45, conduit 46 onto third column 47. Column 47 is generally identical in all respects to column 36. The loading of sample fractions "W"; "$X_1$"; "$X_2$"; and "$X_3$" onto column 47 is shown in FIG. 6b. As the series of further separated sample fractions "W"; "$X_1$"; "$X_2$"; and "$X_3$" leave column 47 after time "$12t_a$" as shown in FIG. 6b, switching valves 41 and 42 are repositioned (as shown in phantom in (FIG. 5) so as to allow entry of the sample fractions into detector 44. The detector response for completely separated fractions "W"; "$X_1$"; "$X_2$"; and "$X_3$" leaving column 47 is shown in FIG. 6c. In this example, the sample bands of interest "$X_1$"; "$X_2$"; and "$X_3$" are well separated after leaving column 47. Fractions can be recycled as many times as necessary through columns 36 and 47, respectively, by appropriate alternate switching of valves 41 and 42, respectively. The process can be continued until resolution is complete, or individual sample fractions begin to overlap onto each other as a result of their continued spreading. Eventually, following completion of the separation, valves 41 and 42, respectively, are positioned to allow the sample-fractions to be diverted to waste 48.

Having thus described the invention, what is claimed and desired to be protected by Letters Patent is presented in the following appended claims:

1. A method of increasing the throughput and separation power of a chromatographic system, which system is operated and fed a series of samples, each sample containing at least one particular constituent of interest, said method comprising the steps of:
    (a) periodically passing a series of samples at a first controlled rate into a first chromatographic column for the purpose of separating a particular constituent of interest from each of said samples;
    (b) obtaining eluant materials for each sample passing from said first chromatographic column and retaining in said chromatographic system only that fraction of each sample containing said particular constituent of interest;
    (c) periodically passing the retained fraction of each sample into a second chromatographic column at a second controlled rate, said first controlled rate being in substantial synchronism with said second controlled rate;
    (d) relating said first and said second controlled rates to provide sufficient separation between the particular constituent of interest of said sample fractions leaving said second chromatographic column and to provide that a number of sample fractions are concurrently passing through said second chromatographic column; and
    (e) passing said sample fractions leaving said second column through at least one additional chromatographic column to recycle said sample fractions and effect a greater separation of constituents in each of said sample fractions.

2. The method of increasing the throughput and separation power of the chromatographic system of claim 1, wherein said chromatographic system is a liquid chromatographic system.

3. The method of increasing the throughput and separation power of the chromatographic system of claim 1, wherein said chromatographic system is a gas chromatographic system.

4. The method of increasing the throughput and separation power of the chromatographic system or claim 1, further comprising the step of:
    analyzing said sample fractions passing from said additional chromatographic column to quantify at least said particular constituent of interest in said sample fractions.

5. The method of increasing the throughput and separation power of the chromatographic system of claim 1, wherein a rate of passing said samples into the first chromatographic column is substantially equal to the rate of passing said sample fractions into said second chromatographic column.

6. The method of claim 1, including the further steps of:
    (e) discontinuing passing of said retained fractions through said second column, recycling each of said fractions leaving said additional column through said second column and analyzing each of said recycled fractions to quantify the amount of at least said particular constituent of interest in said recycled fractions.

7. A system for chromatographic analysis of a series of samples, said apparatus having an improved throughput and separation power comprising:
    a first chromatographic column;
    first means for periodically passing a series of samples into said first chromatographic column at a first controlled rate;
    a second chromatographic column;
    second means for periodically passing a fraction of each sample eluted from said first chromatographic column into said second chromatographic column at a second controlled rate which is in substantial synchronism with said first controlled rate and related to said first controlled rate to provide sufficient separation between particular constituents of interest of each of said sample fractions eluting from said second chromatographic column and to provide that a number of sample fractions are passing concurrently through said second chromatographic column;
    a third chromatographic column for separating eluted fractions passing from said second chromatographic column; and
    recycling means for reintroducing sample fractions passing from said third chromatographic column back through said second chromatographic column.

8. The system for chromatographic analysis of claim 7, further comprising means for analyzing said sample fractions passing from either said second or said third chromatographic column to quantify the amount of the particular constituent of interest in each of said sample fractions.

9. The system for chromatographic analysis of claim 7, wherein the means for analyzing is a photometer.

10. The system for chromatographic analysis of claim 7, wherein the means for analyzing is a spectrophotometer.

11. The system for chromatographic analysis of claim 7, wherein the first means for passing a series of samples through said first chromatographic column comprises a pump and a sample injection valve connected between said pump and said first chromatographic column.

12. The system for chromatographic analysis of claim 7, wherein the second means for passing sample fractions from the first chromatographic column for introduction into said second chromatographic column comprises a switching valve.

13. The system for chromatographic analysis of claim 12, wherein the second means for passing sample fractions through said second chromatographic column further comprises a pump connected to said switching valve.

14. The system for chromatographic analysis of claim 7, wherein said first controlled rate for passing samples into said first chromatographic column is substantially equal to said second controlled rate for passing said sample fractions into said second chromatographic column.

* * * * *